United States Patent [19]

McLaughlin et al.

[11] Patent Number: 5,263,214
[45] Date of Patent: Nov. 23, 1993

[54] RESTRAINT KIT APPARATUS

[76] Inventors: Dean L. McLaughlin, 9296 Guava Ave., Hesperia, Calif. 92345; Michael E. Parsons, 22315 Quivero, Apple Valley, Calif. 92307

[21] Appl. No.: 981,109

[22] Filed: Nov. 24, 1992

[51] Int. Cl.$^5$ ............................ A61G 7/08; A44B 1/04
[52] U.S. Cl. ........................................ 5/628; 24/169; 221/185; 221/276; 206/389; 206/409
[58] Field of Search ............... 206/389, 409; 242/55.2, 242/55.53; 221/185, 276; 5/625, 628; 24/169, 543

[56] References Cited

U.S. PATENT DOCUMENTS

| | | | |
|---|---|---|---|
| 1,946,105 | 2/1934 | Parlett | 242/55.53 |
| 2,237,920 | 4/1941 | Armitt | 242/55.53 |
| 3,091,364 | 5/1963 | Ayres | 221/276 |
| 3,100,932 | 8/1963 | Pipkin | 221/276 |
| 3,737,923 | 6/1973 | Prolo | 5/628 |
| 4,038,726 | 8/1977 | Takabayashi | 24/169 X |
| 4,088,276 | 5/1978 | Littleton | 242/55.53 |
| 4,381,845 | 5/1983 | Feis | 221/185 |
| 4,606,134 | 8/1986 | Flick | 206/409 X |
| 4,610,373 | 9/1986 | Sherbondy | 221/185 X |
| 4,770,299 | 9/1988 | Parker | 206/409 |

*Primary Examiner*—Peter M. Cuomo
*Assistant Examiner*—Michael J. Milano
*Attorney, Agent, or Firm*—Leon Gilden

[57] ABSTRACT

A restraint kit includes a dispensing housing having a clip dispenser therewithin, wherein the dispensing housing is arranged for the selective dispensing of restraint web segments therefrom cooperative with one of a plurality of clip members dispensed from the clip dispenser housing. Web segments cooperative with clip members are secured to an associated back board for the restraint of an individual thereon during a medical emergency situation.

1 Claim, 4 Drawing Sheets

RESTRAINT KIT APPARATUS

BACKGROUND OF THE INVENTION

1. Field of the Invention

The field of invention relates to restraint apparatus, and more particularly pertains to a new and improved restraint kit apparatus wherein the same permits the selective employment of predetermined lengths of restraint web portions, with associated clip structure.

2. Description of the Prior Art

Restraint apparatus of various types have been utilized throughout the prior art indicated by example in U.S. Pat. Nos. 5,014,374; 4,970,739; 4,012,821; and 4,947,418.

The prior art has heretofore utilized restraint structure pre-arranged, wherein the instant invention utilizes dispensing structure in kit form to permit the utilization of disposal web segments that are obtained from a continuous web reel mounted within a web dispensing housing for accommodating individuals of various sizes and physical configurations.

SUMMARY OF THE INVENTION

In view of the foregoing disadvantages inherent in the known types of restraint apparatus now present in the prior art, the present invention provides a restraint kit apparatus utilizing a back board cooperative with a dispenser structure to dispense web segments in association with clip members for use with the back board structure. As such, the general purpose of the present invention, which will be described subsequently in greater detail, is to provide a new and improved restraint kit apparatus which has all the advantages of the prior art restraint apparatus and none of the disadvantages.

To attain this, the present invention provides a restraint kit including a dispensing housing having a clip dispenser therewithin, wherein the dispensing housing is arranged for the selective dispensing of restraint web segments therefrom cooperative with one of a plurality of clip members dispensed from the clip dispenser housing. Web segments cooperative with clip members are secured to an associated back board for the restraint of an individual thereon during a medical emergency situation.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved restraint kit apparatus which has all the advantages of the prior art restraint apparatus and none of the disadvantages.

It is another object of the present invention to provide a new and improved restraint kit apparatus which may be easily and efficiently manufactured and marketed.

It is a further object of the present invention to provide a new and improved restraint kit apparatus which is of a durable and reliable construction.

An even further object of the present invention is to provide a new and improved restraint kit apparatus which is susceptible of a low cost of manufacture with regard to both materials and labor, and which accordingly is then susceptible of low prices of sale to the consuming public, thereby making such restraint kit apparatus economically available to the buying public.

Still yet another object of the present invention is to provide a new and improved restraint kit apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
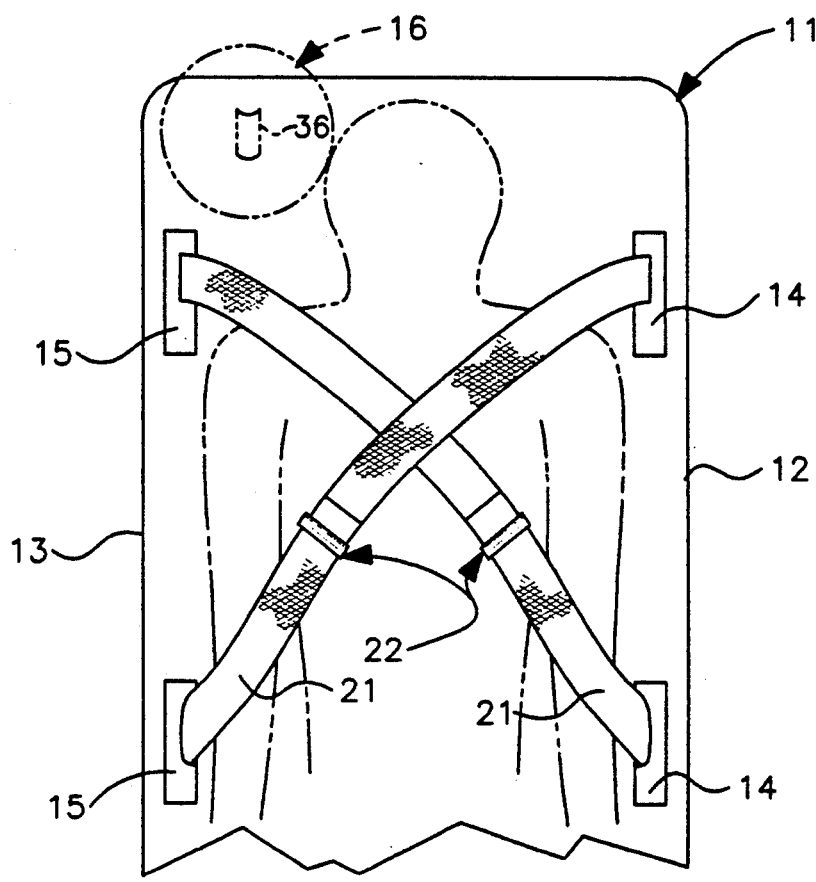
FIG. 1 is an orthographic top view of the back board structure in employment with the use of web segments and associated clip members.
Figure 2:
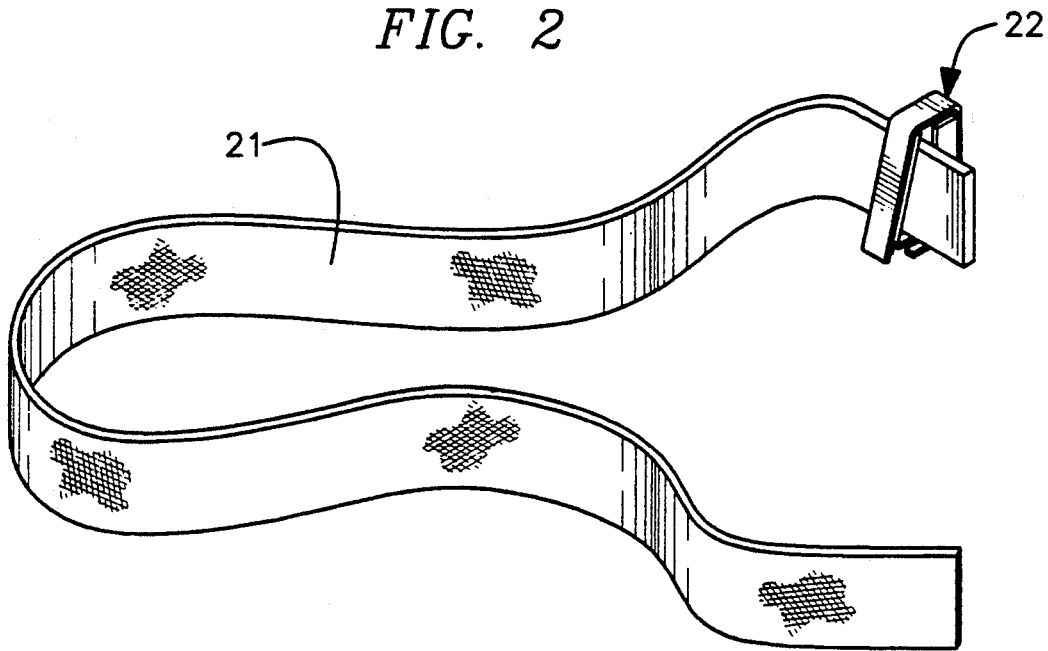
FIG. 2 is an isometric illustration of a web segment and clip structure.
Figure 3:
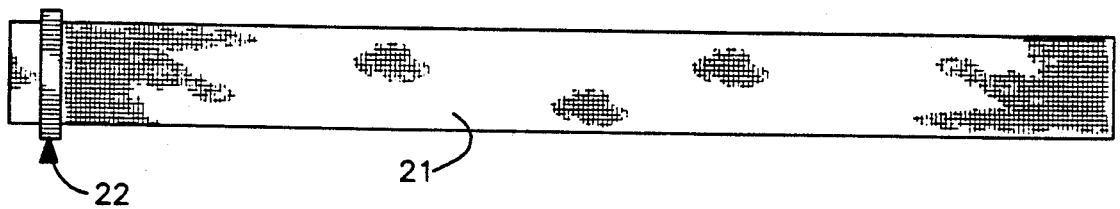
FIG. 3 is an orthographic top view of a restraint web segment.
Figure 4:
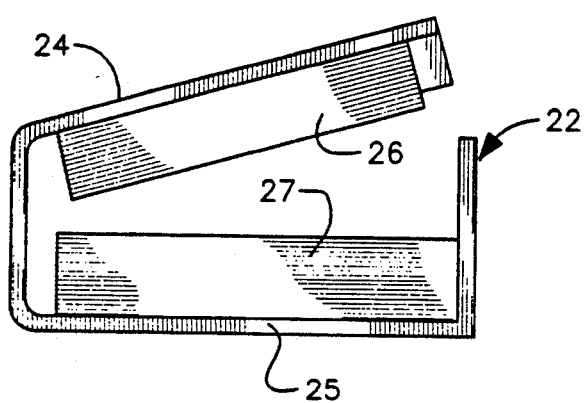
FIG. 4 is an orthographic side view of a clip member.
Figure 4A:
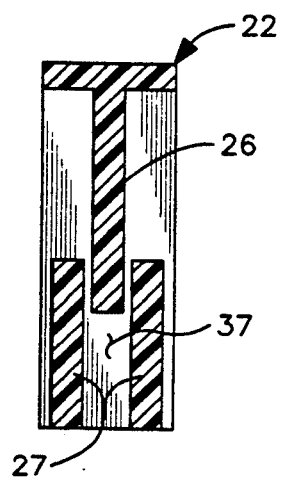
FIG. 4a is an orthographic end view of the clip member as indicated in FIG. 4.

With reference now to the drawings, and in particular to FIGS. 1 to 9 thereof, a new and improved restraint kit apparatus embodying the principles and concepts of the present invention and generally designated by the reference numerals 11–36 will be described.

More specifically, the restraint kit apparatus of the invention essentially comprises a rigid back board 11 having a back board first side spaced from a back board second side in a parallel relationship, with a row of back board first slots 14 directed along the first side 12, with a row of second slots 15 directed along the second side parallel to the first slots 14 arranged for the slots receiving web segments 21 in a manner directed through the slots, with the web segments arranged for simultaneous projection through a first slot of the row of first slots and a second slot of the row of second slots. The web segments 21 are secured together by clip members 22, as indicated in FIG. 1.

Figure 5:
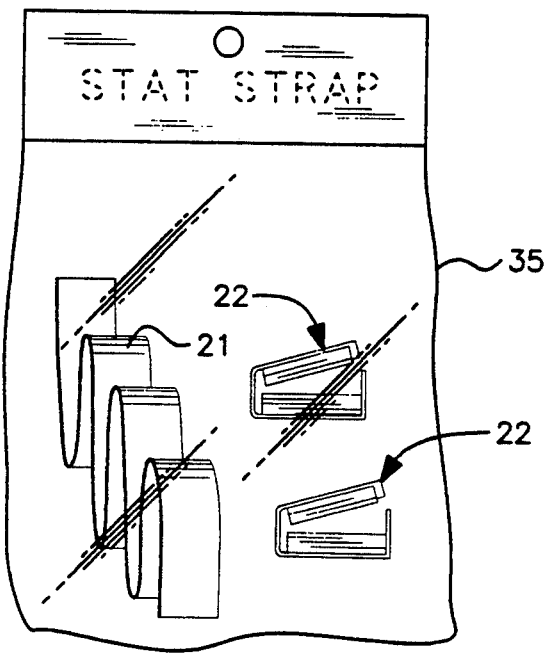
FIG. 5 is an orthographic view of a package containing at least one segment and associated clip members.
Figure 6:
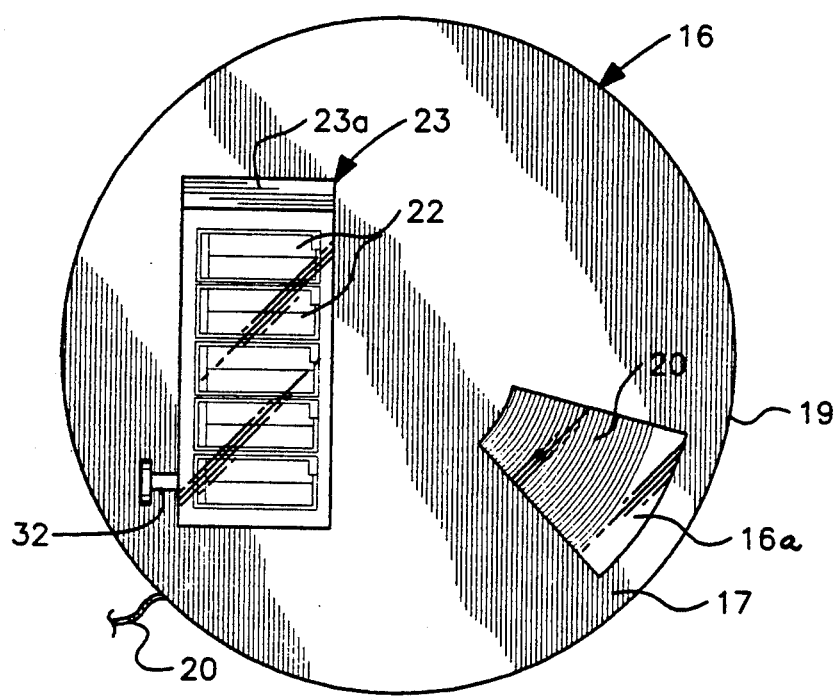
FIG. 6 is an orthographic view of the dispenser housing.
Figure 7:
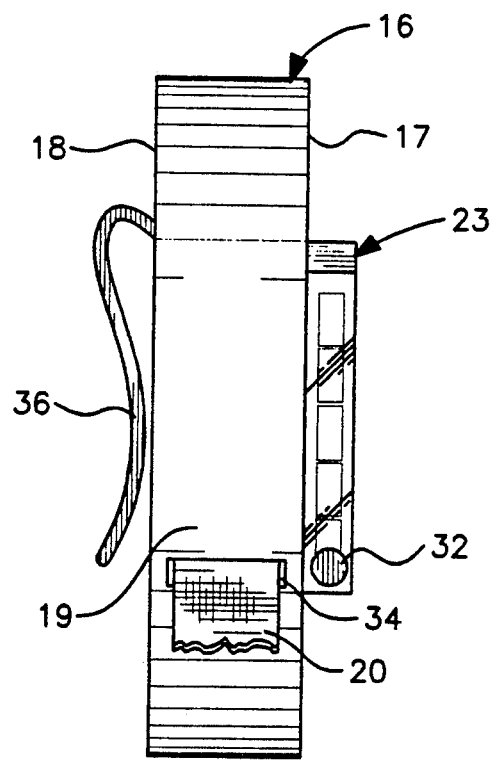
FIG. 7 is an orthographic side view of the dispenser housing.

The kit structure of the invention is arranged to provide for the use of ease of access to the web segments and associated clip members to accommodate various individuals and are positioned upon the back board 11. To this end, at least one, and typically a plurality, of web segments 21 and a plurality of clip members 22 are mounted within a container package 35, as indicated in FIG. 5, for use in cooperation with the back board 11 during emergency situations. In this manner, the segments and clip members are assembled together for securing an individual on the back board. The individual clip members 22 include a first clip leg 24 coextensive with and pivotally mounted to a second clip leg 25. The first clip leg includes a first blade 26 arranged substantially coextensive with the first clip leg, with the second clip leg including a plurality of second leg spaced blades 27 to receive the central blade 26 therebetween. In this manner, the end portions of each of the web segments 21 are positioned between the first leg blade 26 and the second spaced blades 27 to secure the web segment end portions within the gap 37 oriented between the spaced blades 27.

The FIGS. 6–9 indicate a preferred dispensing structure for cooperation and use with the back board 11, wherein a web dispenser housing 16 includes a front wall 17 spaced from and parallel a rear wall 18 having a continuous side wall 19 between the front and rear walls. A flexible continuous restraint web 20 is wound within the web dispenser housing 16 and dispensed through a cylindrical side wall exit opening 34 through the cylindrical side wall 19. In this manner, selective lengths of web segments 21 are severed by any convenient means from the continuous restraint web 20. Removal of one or a plurality of clip members 22 is effected from a transparent clip dispenser housing 23. The transparent clip dispenser housing 23 permits visual observation of a number of clip members 22 remaining within the clip dispenser housing 23, wherein a dispenser housing lid 23a is removably mounted relative to the housing for selective replenishment of the clip members 22 therewithin. Further, a window 16a is directed through the front wall 17 for observation of remaining quantity of restraint web 20 within the web dispenser housing 16.

Figure 8:
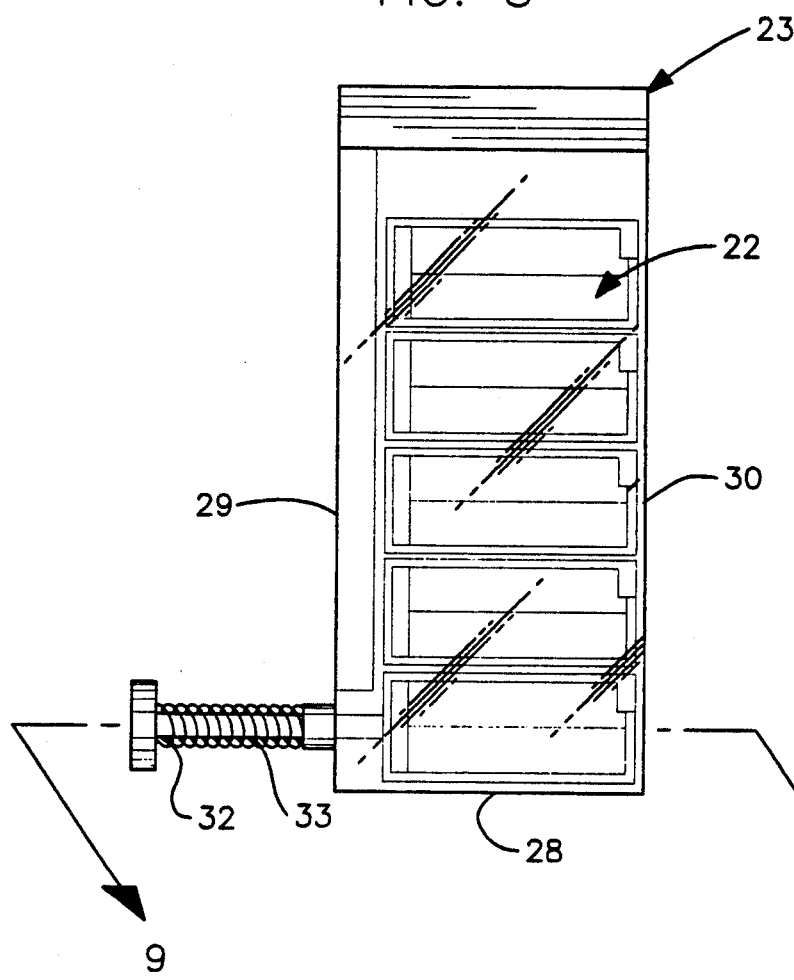
FIG. 8 is an enlarged orthographic view of the clip dispenser housing mounted to the web dispenser housing of FIG. 6 and FIG. 7.
Figure 9:
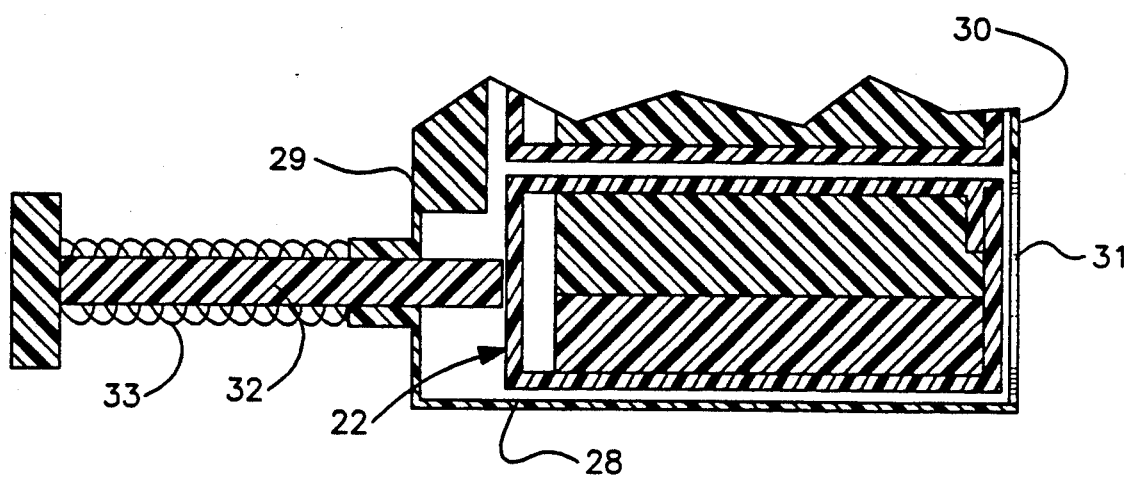
FIG. 9 is an orthographic view, taken along the lines 9—9 of FIG. 8 in the direction indicated by the arrows.

The FIGS. 8 and 9 indicate the clip dispenser housing 23 having a clip housing floor 28, including clip housing first and second side walls 29 and 30. A second side wall opening 31 is arranged to receive a clip member therethrough, wherein a first side wall ejector rod 32 aligned with the second side wall opening 31 is orthogonally and reciprocatably directed through the first side wall 29 for selective displacement and removal of a predetermined number of the clip members 22 from within the clip dispenser housing 23. The ejector rod 32 includes an ejector rod spring 33 to bias the ejector rod in a spaced orientation relative to a clip member 22 positioned upon the floor 28, wherein compression of the spring 33 projects ejector rod 32 into the housing 23 and projection of a clip member 22 through the second side wall opening 31 for use with a web segment 21, in a manner as indicated in FIG. 1.

A spring leg 36 is mounted to the web dispenser housing 16 rear wall 18 for ease of transport and securement of the web dispenser housing 16 onto an individual's torso and the like, and may be secured to the back board 11 if desired for unitary transport and storage of the back board and web dispenser housing.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A restraint kit apparatus, comprising;
 a rigid back board, having a first side spaced from a second side, and
 a row of first slots directed through the back board in adjacency to the first side, and
 a row of second slots directed through the back board in adjacency to the second side, wherein the first slots are parallel to the second slots, and
 a web dispenser housing, the web dispenser housing having a front wall spaced from a rear wall, and
 a cylindrical side wall, with the cylindrical side wall including a side wall exit opening, and
 a continuous flexible restraint web wound within the web dispenser housing, with the rear wall having a spring leg arranged for securement of the back board between the spring leg and the rear wall for ease of transport and storage of the web dispenser housing relative to the back board, and the web dispenser housing includes a transparent window directed through the front wall radially aligned with the front wall for viewing of remaining restraint web of said flexible continuous restraint web within the web dispenser housing, and a transparent clip dispenser housing fixedly mounted to the front wall of the web dispenser housing, wherein the clip dispenser housing includes a lid, and a plurality of clip members positioned within the clip dispenser housing, with the lid arranged for removal relative to the clip dispenser housing for replenishment of said clip members within the clip dispenser housing, and the clip dispenser housing includes a housing first side wall spaced from a housing second side wall, and a housing floor, wherein the housing second side wall includes a side wall opening positioned in adjacency to the floor for receiving one of the clip members therethrough, and the first side wall having an ejector rod, with a spring mounted about the ejector rod between the first side wall and an outer distal end of the ejector rod, with the ejector rod aligned with the second side wall opening, and each of the clip members includes a first clip leg pivotally mounted to a second clip leg, with the first clip leg having a central blade, and the second clip leg having spaced parallel blades defining a gap therebetween, wherein a web segment removed from said restraint web includes web segment end portions, and the end portions are arranged for reception within the gap and secured within the gap for projection of the central blade into the gap.

* * * * *